US006755853B2

(12) United States Patent
McKenzie et al.

(10) Patent No.: US 6,755,853 B2
(45) Date of Patent: *Jun. 29, 2004

(54) METHODS AND KITS FOR THE INHIBITION OF HYPERPLASIA IN VASCULAR FISTULAS AND GRAFTS

(75) Inventors: John R. McKenzie, San Carlos, CA (US); Robert F. Zuk, Atherton, CA (US); Axel F. Brisken, Fremont, CA (US); Paul D. Corl, Palo Alto, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 10/010,411

(22) Filed: Dec. 5, 2001

(65) Prior Publication Data

US 2002/0077694 A1 Jun. 20, 2002

Related U.S. Application Data

(63) Continuation of application No. 09/345,661, filed on Jun. 30, 1999, now Pat. No. 6,387,116.

(51) Int. Cl.[7] .......................... A61F 2/06; A61B 17/20; A61B 17/22
(52) U.S. Cl. .......................... 623/1.1; 604/22; 606/128
(58) Field of Search ................................ 623/1.15, 1.1, 623/1.12, 1.13; 604/22, 507; 606/108, 169, 194, 195, 128, 110, 41; 600/504, 505

(56) References Cited

U.S. PATENT DOCUMENTS

| | | | |
|---|---|---|---|
| 4,840,940 A | 6/1989 | Sottiurai | |
| 5,059,166 A | 10/1991 | Fischelle et al. | |
| 5,078,736 A | 1/1992 | Behl | |

(List continued on next page.)

FOREIGN PATENT DOCUMENTS

| | | | |
|---|---|---|---|
| GB | 2321853 | 12/1998 | |
| WO | WO 98/48711 | 11/1998 | |
| WO | WO01/70112 A1 * | 9/2001 | .................. 600/437 |

OTHER PUBLICATIONS

Beathard, A. Gerald "Gianturco self–expanding stent in the treatment of stenosis in dialysis access grafts" *Kidney International*, vol. 43, pp. 874–877 (1993).

Gray, Richard J., et al. "Use of Wallstents for Hemodialysis Access–related Venous Stenoses and Occlusions Untreatable with Balloon Angioplasty" *Radiology* 195: 479–484 (1995).

He, D.S. et al., "Application of ultrasound energy for intracardiac ablation of arrhythmias" *European Heart Journal* 16:961–966, (1995).

(List continued on next page.)

*Primary Examiner*—A. Stewart
(74) *Attorney, Agent, or Firm*—Townsend and Townsend and Crew LLP (57) ABSTRACT

A method for inhibiting hyperplasia at an anastomotic junction of a vascular fistula or vascular graft comprises exposing the anastomotic junction to vibrational energy at a mechanical index and for a time sufficient to inhibit hyperplasia. Kits are described comprising the catheter or a probe suitable for performing the methods together with instructions for use setting forth the methods. The methods and kits are particularly suitable for treating anastomotic junctions formed to provide vascular access for hemodialysis, hemofiltration, and the like. The methods and kits are also suitable for treating other vascular grafts, such as those formed during cardiac bypass graft surgery, vascular repair, and the like.

15 Claims, 6 Drawing Sheets

U.S. PATENT DOCUMENTS

| | | | |
|---|---|---|---|
| 5,199,939 A | | 4/1993 | Dake et al. |
| 5,302,168 A | | 4/1994 | Hess |
| 5,315,998 A | | 5/1994 | Tachibana et al. |
| 5,318,014 A | | 6/1994 | Carter |
| 5,362,309 A | | 11/1994 | Carter |
| 5,443,495 A | | 8/1995 | Buscemi et al. |
| 5,512,291 A | * | 4/1996 | Li .............................. 424/443 |
| 5,616,114 A | | 4/1997 | Thornton et al. |
| 5,620,409 A | | 4/1997 | Venuto et al. |
| 5,755,778 A | | 5/1998 | Kleshinski |
| 5,836,896 A | | 11/1998 | Rosenschein |
| 5,875,782 A | * | 3/1999 | Ferrari et al. ............... 128/898 |
| 5,902,263 A | | 5/1999 | Patterson et al. |
| 5,914,345 A | | 6/1999 | Slepian et al. |
| 6,015,387 A | | 1/2000 | Schwartz et al. |
| 6,053,873 A | | 4/2000 | Govari et al. |
| 6,070,094 A | | 5/2000 | Swanson et al. |
| 6,071,956 A | | 6/2000 | Slepian et al. |
| 6,086,573 A | | 7/2000 | Siegel et al. |
| 6,170,488 B1 | * | 1/2001 | Spillman et al. ............ 128/899 |
| 6,210,393 B1 | * | 4/2001 | Brisken ...................... 604/508 |
| 6,296,619 B1 | * | 10/2001 | Brisken et al. ................ 604/22 |
| 6,361,554 B1 | * | 3/2002 | Brisken ...................... 623/1.1 |
| 6,387,116 B1 | * | 5/2002 | McKenzie et al. ............ 623/1.1 |
| 6,464,680 B1 | * | 10/2002 | Brisken et al. ............. 604/501 |
| 6,494,874 B1 | * | 12/2002 | Brisken |
| 6,499,487 B1 | * | 12/2002 | McKenzie et al. .......... 128/898 |
| 6,503,243 B1 | * | 1/2003 | Brisken ...................... 604/508 |

OTHER PUBLICATIONS

Johnstone, P.A.S. et al., "Effects of Intraoperative Radiotherapy on Vascular Grafts in a Canine Model" *Int'l J. Radiation Oncology Biol. Phys.*, vol. 29, No. 5, pp. 1015–1025, (1994).

Kaufman, Gary E., et al., "Lysis and Viability of Cultured Mammalian Cells Exposed to 1MHz Ultrasound" *Ultrasound in Med. & Biol.*, vol. 3, pp. 21–25, (1977).

Rosenschein, Uri MD et al., "Experimental Ultrasonic Angioplasty: Disruption of Atherosclerotic Plaques and Thrombi in Vitro and Arterial Recanalization in Vivo" *JACC* vol. 15, No. 3, (Mar. 1, 1990).

Siegel, Robert J. MD et al., "Ultrasound Angioplasty" *Review*, vol. 3, No. 3, pp. 135–143 (May/Jun. 1991).

Taber, T.E. et al., "Maintenance of Adequate Hemodialysis Access Prevention of Neointimal Hyperplasia" *ASAIO Journal* pp. 41:842–846 (1995).

* cited by examiner

METHODS AND KITS FOR THE INHIBITION OF HYPERPLASIA IN VASCULAR FISTULAS AND GRAFTS

CROSS-REFERENCES TO RELATED APPLICATIONS

This application is a continuation of application Ser. No. 09/345,661, filed on Jun. 30, 1999, now U.S. Pat. No. 6,387,116B1, the full disclosure of which is incorporated herein by reference. The subject matter of the present invention is related to the disclosure of copending application Ser. No. 09/223,230, now U.S. Pat. No. 6,210,393B1, the full disclosure of which is incorporated herein by reference.

BACKGROUND OF THE INVENTION

1. Field of the Invention

The present invention relates generally to medical methods, systems, and kits. More particularly, the present invention relates to methods for treating vascular fistulas and grafts to inhibit hyperplasia and subsequent occlusion thereof.

Vascular fistulas and grafts are used in a wide variety of circumstances when it is desired to reconfigure or re-establish vascular circulation in a patient. For example, both fistulas and grafts are used to create access sites for blood withdrawal and return in patient's undergoing periodic kidney dialysis, hemofiltration, or other extracorporeal blood treatments. Usually, either a native artery and vein are connected together via a side-to-side anastomosis or a saphenous vein or synthetic graft is placed between an artery and a vein and attached at each end via an end-to-side anastomosis. Both natural grafts (usually a vein harvested from the patient being treated) and synthetic grafts are used in open and/or minimally invasive surgical procedures for treating vascular disorders, such as coronary artery bypass grafting for treating heart disease, surgical graft introduction for treating abdominal aortic aneurysms, peripheral vasculature repair, and the like. In all cases, at least two anastomotic connections are required for implanting the graft.

In many cases, it has been found that the anastomotic junction which is created at the fistula or between the blood vessel and the implanted graft is at significant risk of occlusion due to hyperplasia. In particular, intimal hyperplasia of the vascular smooth muscles cells will often occur as an injury response to the surgical creation of the anastomosis. Occlusion resulting from the hyperplasia is exacerbated by thrombosis which occurs as a result of the blood flow turbulence at the site of the anastomosis. The most troublesome lesions are formed at anastomotic junctions between a graft or artery and a vein.

At present, there are no effective treatments for hyperplasia at anastomotic junctions in any of the cases discussed above. When the anastomotic junction in an arterio-venous (A-V) fistula or graft fails in a dialysis patient, it is necessary create a new dialysis access site. After a time, there are no more new sites and kidney dialysis is no longer available to the patient. While it is possible for heart bypass patients having failed grafts to redo the procedure, second and later procedures are seldom as effective in treating the disease as in an initial bypass procedure. Moreover, the availability of autologous blood vessels for performing the procedure places a limit on the number of procedures that can be performed.

For all of these reasons, it would be desirable to provide methods, systems, and kits, for treating anastomotic junctions which are formed as the result of the creation of an arterio-venous fistula or the implantation of a bypass or other graft in a patient's vasculature. It would be particularly desirable to provide methods suitable for treating anastomotic junctions both at the time they are created as well as at subsequent times in order to effectively inhibit hyperplasia at the junctions. Preferably, the methods for inhibiting hyperplasia would require little or no modification to the implantation techniques themselves and would be suitable for use in a wide variety of procedures which rely on the formation of anastomotic attachments, including at least all of those described above. At least some of these objectives will be met by the inventions described hereinafter.

2. Description of the Background Art

The failure of vascular grafts and fistulas used for hemodialysis access is recognized to stem at least in part from neointimal hyperplasia. See, Taber et al. (1995) ASAIO J 41:842–846. Both pharmacological and mechanical solutions have been proposed. See, e.g., U.S. Pat. No. 4,840,940, which proposes systemic administration of fractionated heparin to inhibit restenosis, and Gray et al. (1995) Radiology 195:479–484, and Beathard (1993) Kidney Int. 43:872–877, which describe the use of stents for maintaining patency in arterio-venous access sites. Johnstone et al. (1994) Int. J. Radiat. Oncol. Biol. Phys. 29:1015–1025, observed the effects of intraoperative radiotherapy and external beam radiotherapy on prosthetic vascular grafts in a canine model and found that radiation could contribute to late occlusion of the graft.

Intravascular inhibition of hyperplasia by exposure to radioisotopes is described in a number of patents and publications, including U.S. Pat. Nos. 5,616,114; 5,302,168; 5,199,939; and 5,059,166. The therapeutic application of ultrasonic energy is described in a number of patents and publications including U.S. Pat. Nos. 5,362,309; 5,318,014; 5,315,998, WO 98/48711; and others. The application of intravascular ultrasound for inhibiting restenosis by decreasing the migration, viability, and adhesion of vascular smooth muscle cells via a cavitation mechanism is suggested in U.S. Pat. No. 5,836,896. See also, Rosenchein et al. (1990) JACC 15:711–717, and Siegel et al. (1991) J. Invasive Cardiol. 3:135, which describe thrombolysis via the cavitation mechanism. A high frequency ultrasonic catheter intended for tissue ablation which employs an air-backed transducer is described in He et al. (1995) Eur. Heart J. 16:961–966. Cell lysis of mammalian cell lines maintained in vitro is described in Kaufman et al. (1977) Ultrasound Med. Biol. 3:21–25. Catheters suitable for performing at least some methods according to the present invention are described in copending application nos. 08/565,575; 08/566,740; 08/566,739; 08/708,589; 08/867,007, and 09/223,225, filed on Dec. 30, 1998, and assigned to the assignee of the present invention, the full disclosures of which are incorporated herein by reference.

BRIEF SUMMARY OF THE INVENTION

The present invention provides methods and kits for inhibiting hyperplasia at an anastomotic junction of a vascular graft or fistula. By "hyperplasia," it is meant that excessive cell proliferation occurs at the anastomotic junction (attachment site) between an artery and a vein in the case of a fistula, and an artery or vein and a tubular graft in the case of a graft connection. Hyperplasia can occur as the result of surgical creation of the anastomotic junction, and it has been found that the surgical attachment can damage cells lining the involved blood vessels in a manner which results in an injury response characterized by secretion of extracellular matrix and excessive proliferation of the smooth muscle cells lining the blood vessels which together form the neointimal layer lining the blood vessel wall adjacent the anastomotic junction.

Treatment according to the present invention is effected by exposing the anastomotic junction to vibrational energy at a mechanical index and for a time sufficient to inhibit hyperplasia of smooth muscle cells within the neointimal layer of the blood vessel. Surprisingly, it has been found that the strength of vibrational energy (as measured by the mechanical index) and the duration of the treatment (as measured by elapsed treatment time, duty cycle, and pulse repetition frequency (PRF)) can be selected to provide highly effective hyperplasia inhibition in the neointimal layer without significant damage to surrounding tissues or structures within the blood vessel(s) and/or the anastomotic junction itself. In particular, by exposing an anastomotic junction at risk of neointimal hyperplasia to a vibrational energy having a mechanical index in the range from 0.1 to 50, preferably from 0.2 to 10, and more preferably from 0.5 to 5, for a treatment time in the range from 10 seconds to 1000 seconds, preferably from 30 seconds to 500 seconds, and more preferably from 60 seconds to 300 seconds, the proliferation of vascular smooth muscle cells in the neointimal layer of the artery can be reduced by at least 2% (in comparison with untreated controls) after seven days, often at least 4%, and sometimes 6% or greater. The resulting reduction in hyperplasia mass after 28 days will typically be at least 10%, usually at least 20%, and preferably at least 30%. Such inhibitions can be achieved without significant necrosis of the smooth muscle cells.

The methods of the present invention will preferably be performed under conditions which cause little or no cavitation within the smooth muscle cells and other cells within or near the treatment region. While the initiation of cavitation will be governed to a large extent by the power and mechanical index of the vibrational energy, the presence of cavitation nucleii, such as gas microbubbles, can also contribute to cavitation. Thus, the methods of the present invention will preferable be performed in the absence of introduced microbubbles and/or other cavitation nucleii. Moreover, the treatment conditions of the present invention will result in little or no inhibition of migration of smooth muscle cells into the neointimal layer. Instead, the migration will be generally normal, but the migrated cells will have a quiescent phenotype rather than the proliferative phenotype associated with the formation of neointimal hyperplasia. In their proliferative phenotype, vascular smooth muscle cells not only divide rapidly but also excrete extracellular matrix which accounts for most of the volume of the neointimal layer responsible for hyperplasia. Quiescent smooth muscle cells divide less rapidly, do not secrete significant amounts of extracellular matrix, and promote healing and reformation of an intact endothelial layer over the neointimal layer. Additionally, the duty cycles and pulse repetition frequencies of the treatment will be selected to limit the heating within the neointimal layer to a temperature rise below 10° C., preferably below 5° C., and more preferably below 2° C. Such limited temperature rise further assures the viability and normalcy of the treated cells to enhance healing and re-endothelialization of the neointimal layer in a rapid manner.

Anastomotic junctions will be formed in a patient's vasculature by various surgical interventions, such as fistula creation, arterio-venous (AV) graft implantation, cardiopulmonary graft implantation, vascular repairs (such as implantation of a graft to treat aneurysms in the abdominal aorta and elsewhere), coronary and peripheral bypass grafting, carotid patch grafting, and the like. Fistulas will most commonly be created between a native artery and native vein in order to form a point of high blood flow for circulatory access, most commonly for hemodialysis, hemofiltration, or the like, but also for other extracorporeal circulation treatment protocols. Such fistulas may be formed by side-to-side anastomosis, end-to-side anastomosis, and end-to-end anastomosis. The surgical procedures for forming such anastomotic junctions are well described in the medical and patent literature. See, for example, *Vascular Diseases: Surgical & Interventional Therapy*, Strandness, Jr., and Bred, Eds., Churchill Livingstone, N.Y., Chapter 73. Graft implantation may be for a variety of purposes, including vascular access, vascular bypass, and vascular repair. In general, graft implantation involves implanting a tubular prosthesis, typically autologous blood vessel harvested from the patient being treated, a non-autologous vessel harvested from a human donor, or a synthetic graft, typically formed from a material such as polyester, PTFE, or the like, which may be reinforced, laminated, or otherwise treated to improve mechanical and biological characteristics. In the case of bypass procedures, the grafts will usually be attached by end-to-side, or side-to-side anastomoses to a single blood vessel, typically an artery. In the case of vascular repair, the graft will frequently replace a diseased portion of the blood vessel, frequently being attached by end-to-end anastomoses to replace a segment which has been surgically removed. For vascular access, the graft will usually be attached by end-to-side anastomoses between an artery and a vein. In the latter case, intimal hyperplasia has been a particular problem at the anastomotic junction formed between the graft and the vein. The formation of such graft attachments is also well described in the patent and medical literature. See, *Vascular Diseases: Surgical & Interventional Therapy, supra*. Chapter 74.

Treatment according to the present invention will usually be performed immediately following or shortly after surgical creation of the anastomotic junction. The treatment can be performed intravascularly (by introducing a probe or catheter into the lumen of the anastomotic junction), by direct placement of an acoustic probe over the exterior of the junction (usually through the surgical incision which has been formed to create the junction), by external application of acoustic energy on the patient's skin after the surgical incision has been closed, or as a combination of these approaches. By "substantially immediately" after the formation of the anastomotic junction, it is meant that the treatment will occur either while the surgical incision remains open or shortly after the surgical incision is closed, typically within one hour or less.

Alternatively or in addition to such immediate treatment, the present invention also provides for treatment of the anastomotic junctions in the hours, days, and weeks following the initial implantation of the graft or formation of fistula. In some instances, it will be desirable to perform the treatment protocols of the present invention indefinitely, typically at periodic intervals, to provide continuing prophylactic inhibition of hyperplasia at the junction(s). In one aspect of the present invention, treatment will be applied one or more times during the period from one day to one week following the surgical procedure which formed the anastomotic junction. It is presently believed that hyperplastic activity peaks at a time approximately several days after the initial vascular injury and that the inhibitory exposure of an anastomotic junction to vibrational energy during the expected peak of hyperplastic activity will be particularly beneficial. When performed after closure of the surgical site, vibrational energy will usually be applied using an intravascular catheter, generally as described in copending application Ser. No. 09/223,230. Alternatively, vibrational energy could be applied using a surface device, such as described in copending application Ser. Nos. 09/255,290. The full disclosures of both of these copending applications are incorporated herein by reference.

In addition to the use of vibrational energy for inhibiting hyperplasia, the present invention includes the optional administration of biologically active substances which will further inhibit hyperplasia, preferably in a synergistic manner with the use of vibratory energy. For example, genes, such as those encoding vascular endothelial growth factor (VEGF) may be administered locally or systemically at the time of the use of vibrational energy. Drugs, such as thrombolytic drugs (streptokinase, urokinase, and TPA, etc.) and/or anti-thrombotic drugs (e.g., heparin, hirudin, hirulog, etc.) may also be administered concurrently with the vibrational therapy.

Mechanical index and duration of the treatment are the most important treatment parameters. The mechanical index (MI) is a function of both the intensity and the frequency of the vibrational energy produced, and is defined as the peak rarefactional pressure (P) expressed in megaPascals divided by the square root of frequency (f) expressed in megaHertz:

$$MI = \frac{P}{\sqrt{f}}$$

The duration of treatment is defined as the actual time during which vibrational energy is being applied to the arterial wall. Duration will thus be a function of the total elapsed treatment time, i.e., the difference in seconds between the initiation and termination of treatment; burst length, i.e., the length of time for a single burst of vibrational energy; and pulse repetition frequency (PRF). Usually, the vibrational energy will be applied in short bursts of high intensity (power) interspersed in relatively long periods of no excitation or energy output. An advantage of the spacing of short energy bursts is that heat may be dissipated and operating temperature reduced.

Broad, preferred, and exemplary values for each of these parameters is set forth in the following table.

| PREFERRED AND EXEMPLARY TREATMENT CONDITIONS | | | |
|---|---|---|---|
| | BROAD | PREFERRED | EXEMPLARY |
| Mechanical Index (MI) | 0.1 to 50 | 0.2 to 10 | 0.5 to 5 |
| Intensity (SPTA, W/cm$^2$) | 0.01 to 100 | 0.1 to 20 | 0.5 to 5 |
| Frequency (kHz) | 20 to 5000 | 300 to 3000 | 500 to 1500 |
| Elapsed Time (sec.) | 10 to 900 | 30 to 500 | 60 to 300 |
| Duty Cycle (%) | 0.1 to 100 | 0.2 to 10 | 0.2 to 2 |
| Pulse Repetition Frequency (PRF) (Hz) | 10 to 10,000 | 100 to 5000 | 300 to 3000 |

The methods of the present invention may further find use in combination with other protocols for recanalizing an anastomotic junction after it has become at least partly occluded. Recanalization may be achieved using conventional techniques, particularly angioplasty, atherectomy, laser angioplasty, or other catheter-based interventional technique. Following the recanalization intervention, the anastomotic junction will be treated with vibrational energy according to the methods described above. The junction may be exposed to the vibrational energy immediately following the recanalization protocol or at various times following the protocol. For example, it may be particularly desirable to expose the anastomotic junction to the vibrational energy at a time from one day to one week following the recanalization protocol. In such cases, use of an external probe will often be desired. When the vibrational energy is applied immediately following the recanalization protocol, use of an intravascular catheter for applying the vibrational energy will be more feasible and more frequently preferred.

In addition to the methods described above, the present invention further comprises kits for performing these methods. The kits will include a vibrational transducer, typically in the form of a probe, external device, catheter, or the like, together with instructions for use setting forth any of the methods described above. Optionally, kits may further include conventional packaging such as a pouch, tray, box, tube, or the like. The instructions may be provided on a separate printed sheet, e.g., a package insert setting forth the instructions for use, or may be printed in whole or in part on the packaging. A variety of other kit components could also be included, such as drugs, genes, and the like, for concurrent administration to the patient. Usually, at least some of the kit components will be maintained in a sterile manner within the packaging.

DETAILED DESCRIPTION OF THE INVENTION

Anastomotic junctions between blood vessels and/or a blood vessel and a biological or synthetic graft are subject to occlusion due to hyperplasia and other injury responses, as discussed above. The present invention relies on exposure of such anastomotic junctions to vibrational energy at a mechanical index, and for a time sufficient to inhibit hyperplasia and thus reduce the risk of occlusion of the anastomotic junction and failure of the graft or fistula which has been created. The vibrational energy can be directed at the anastomotic junction in a variety of ways and at a variety of different times. When surgical access is available, e.g., at the time of fistula creation or graft implantation, it will often be desirable to apply the vibrational energy directly to an exterior surface of the junction using a probe or other suitable acoustic generator. It will be appreciated that the probe can be engaged directly against the surface of the blood vessels or blood vessel and graft. When surgical access is not available, the vibrational energy can be provided using an intravascular catheter introduced to the patient's vasculature and advanced to the anastomotic junction or junctions using conventional guidewire and fluoroscopic techniques. The ultrasonic energy can then be directed at the anastomotic junction from the interior of the blood vessel, usually in a radially outward direction. If surgical access is unavailable and catheter access is undesirable, it will be possible to focus acoustic energy through the patient's skin to the anastomotic junction(s). A suitable external probe can be placed on the skin over the junction site and acoustic energy of the desired frequency, intensity, and mechanical index applied through the overlying skin. In some instances, it will be desirable to combine two or more of these specific approaches in order to optimize treatment.

The application of vibrational energy according to the methods of the present invention may be performed at various times during and after graft implantation or fistula formation. Vibrational energy will frequently be applied immediately after graft implantation or fistula formation using a probe which is introduced through a surgical access site, as described above. After the surgical site is closed, it will frequently be desirable to apply vibrational energy in the period from one day to one week following the surgical procedure. It is presently believed that hyperplastic activity is at a peak approximately several days after the initial procedure. The therapeutic use of vibrational energy according to the present invention may be applied at any other time when it is believed that the anastomotic junction is at risk of hyperplasia. In some instances, it will be desirable to perform the vibrational treatments periodically, e.g., daily, weekly, monthly, or at other regular intervals. It may also be desirable to apply the vibrational inhibition methods of the present invention in conjunction with other interventions for clearing established occlusion at anastomotic junctions. For example, the methods of the present invention may be used following angioplasty, atherectomy, laser angioplasty, or other intravascular procedures for reducing or removing stenotic material within an anastomotic junction.

A variety of specific procedures employing the principles of the present invention will now be described. It will be appreciated that these specific procedures are meant to be exemplary and that the present invention may be applied to virtually any surgical procedure which results in the surgical creation of an anastomotic junction within a patient's vasculature.

Figure 1:
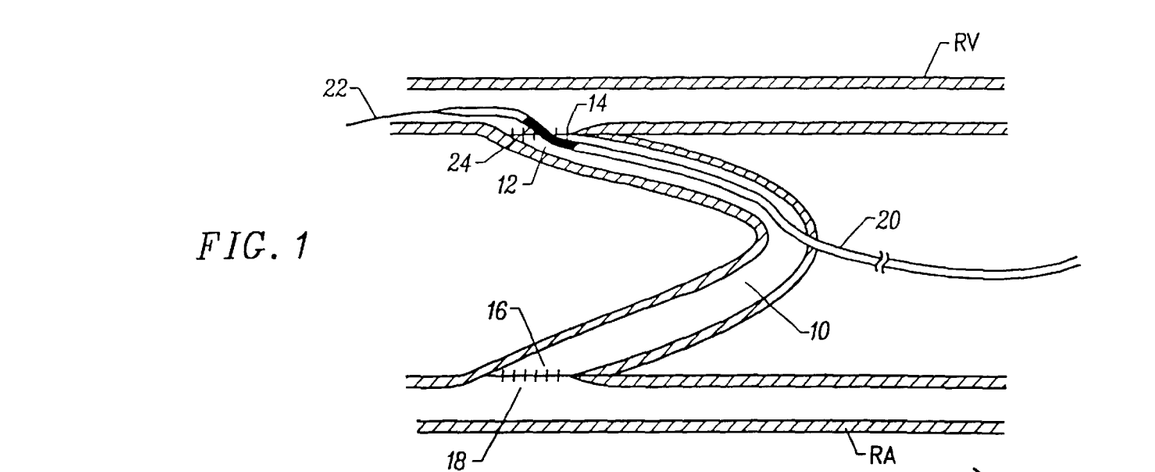
FIGS. 1 and 2 illustrate alternative treatment protocols according to the methods of the present invention for inhibiting hyperplasia at end-to-side anastomoses created in forming a graft between a radial artery and a radial vein for hemodialysis access.
Figure 2:
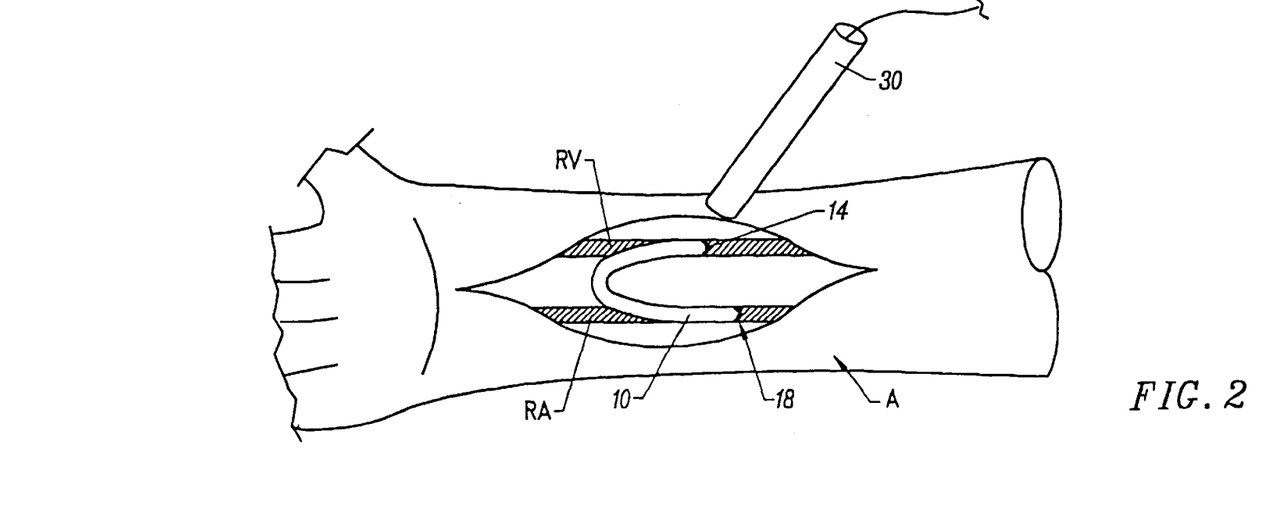

Referring now to FIGS. 1 and 2, hemodialysis access is frequently provided by placing a graft between a radial artery RA and a radial vein RV in a patient's arm. The graft may be made from a vessel harvested from the patient or from a human donor, or may be a tubular synthetic graft formed from polyester, PTFE, or the like. The graft 10, referred to as an arterio-venous shunt, is connected at one end 12 via an end-to-side anastomotic junction 14 and at the other end 16 via an end-to-side anastomotic junction 18. In a first exemplary treatment protocol (FIG. 1), an intravascular catheter 20 may be introduced into the graft 10 over a guidewire 22. A suitable ultrasonic transducer 24 on the catheter 20 may then be positioned within the anastomotic junction 14. The transducer 24 will then be energized to deliver vibrational energy within the parameters set forth above. Use of the intravascular catheter 20 may occur at any time from the initial implantation of the graft (even prior to incision closure) to after closure of the incision in the days, weeks, and months, following implantation. Use of the catheter 20 will be particularly suitable for treatment of either anastomotic junction after treatment with angioplasty, atherectomy, or the like. An alternative treatment of the anastomotic junction 16 using a vibrational probe 30, is illustrated FIG. 2. The probe 30 is introduced through the incision in the arm used to initially implant the graft 10. Initially, the junctions 14 and 18 may also be treated using an external probe after the incision has been closed, although this particular approach is not illustrated.

Figure 3:
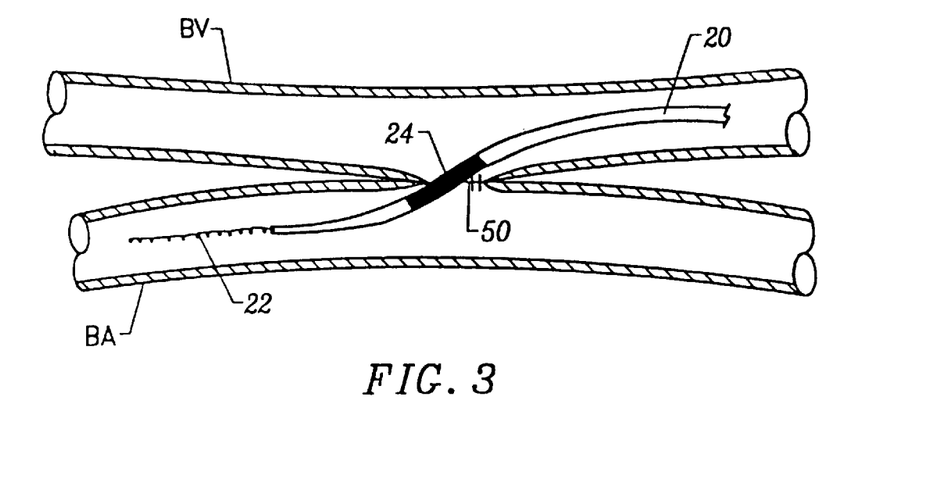
FIGS. 3 and 4 illustrate alternative treatment protocols for a side-to-side arterio-venous fistula between a brachial artery and basilic vein in the arm.
Figure 4:
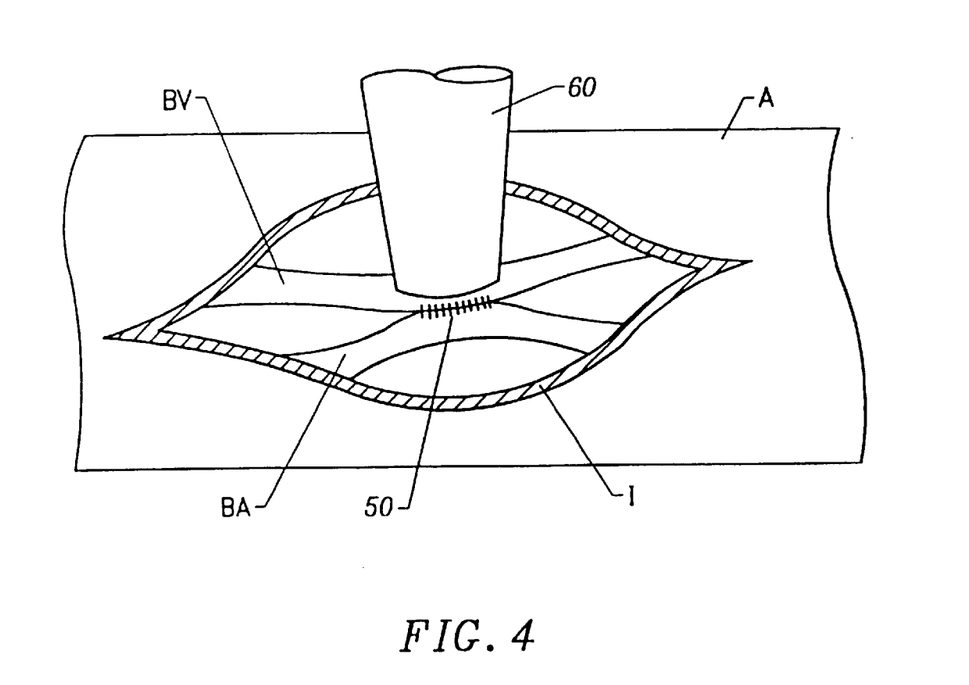

Referring now to FIGS. 3 and 4, treatment of a side-to-side anastomotic junction 50 formed between a brachial artery BA and a basilic vein BV is described. The anastomotic junction 50 may be formed by conventional surgical techniques, usually through an incision I in the arm as illustrated in FIG. 4. After the junction 50 is formed, it may be treated, either using an intravascular catheter 20 introduced over a guidewire 22 where an ultrasonic transducer 24 is located within the junction (FIG. 3). The junction is then treated with vibrational energy by energizing the transducer, generally as described above. Alternatively or additionally, the junction 50 may be treated with an external probe 60 while the incision remains open (FIG. 4).

Figure 5:
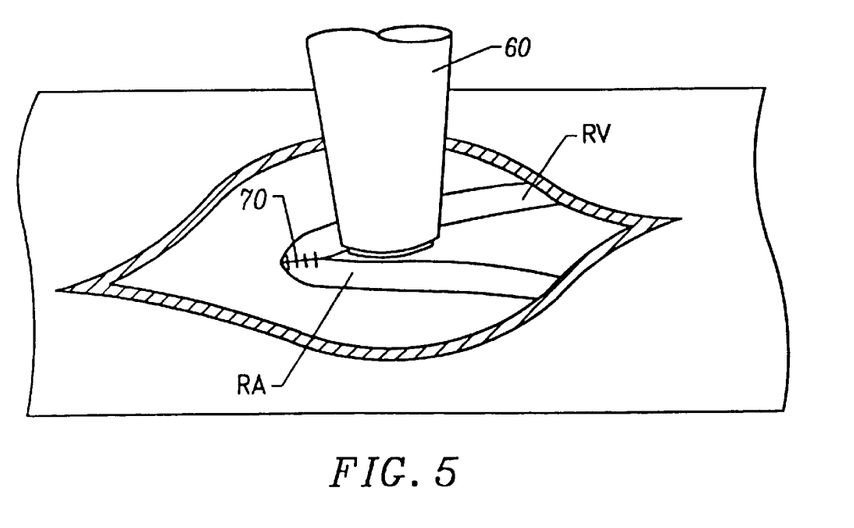
FIG. 5 illustrates treatment according to the present invention of an end-to-end anastomosis forming a fistula between a radial artery and a radial vein in the arm.

Treatment of an end-to-end anastomotic junction 70 between a radial artery RA and a radial vein RV is illustrated in FIG. 5. While use of an ultrasonic probe 60 is shown, it will be appreciated that use of an intravascular catheter or other external probe could also be used.

Figure 6:
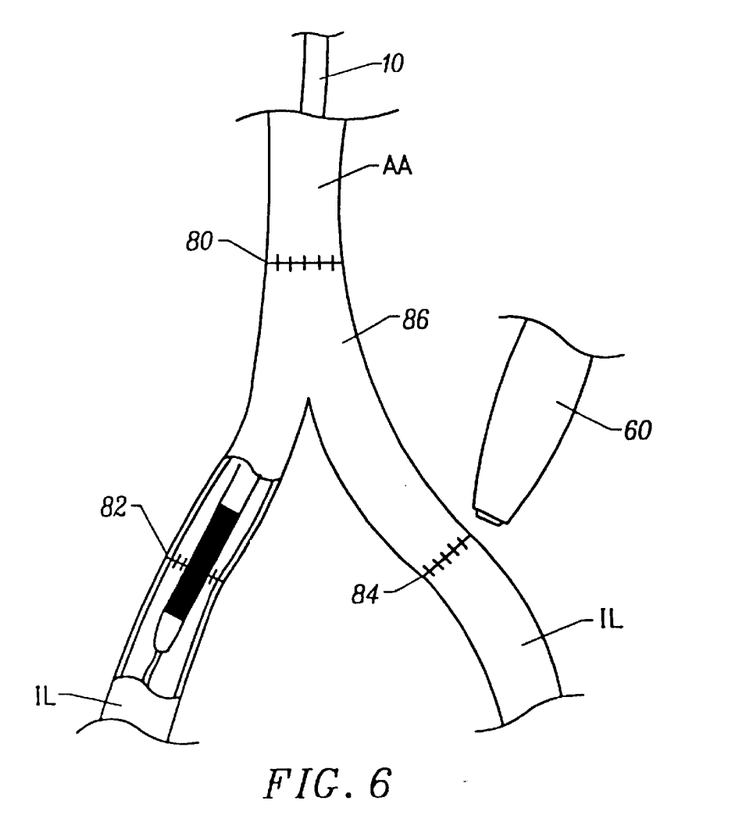
FIG. 6 illustrates treatment of the anastomotic junctions in an aortic graft of the type used to treat an abdominal aortic aneurysm according to the present invention.

Referring now to FIG. 6, the methods of the present invention can be used to treat the anastomotic junctions 80, 82, and 84, which are formed when a graft 86 is implanted in the abdominal aorta AA to connect to the right and left iliacs IL. As shown, a catheter 10 can be used to treat any of the anastomotic junctions 80, 82, or 84. Alternatively or additionally, a probe 60 can be used to treat the outsides of these junctions while a surgical incision remains open. Additionally, external probes may be used on the surface of the skin after the incision has been closed.

Figure 7:
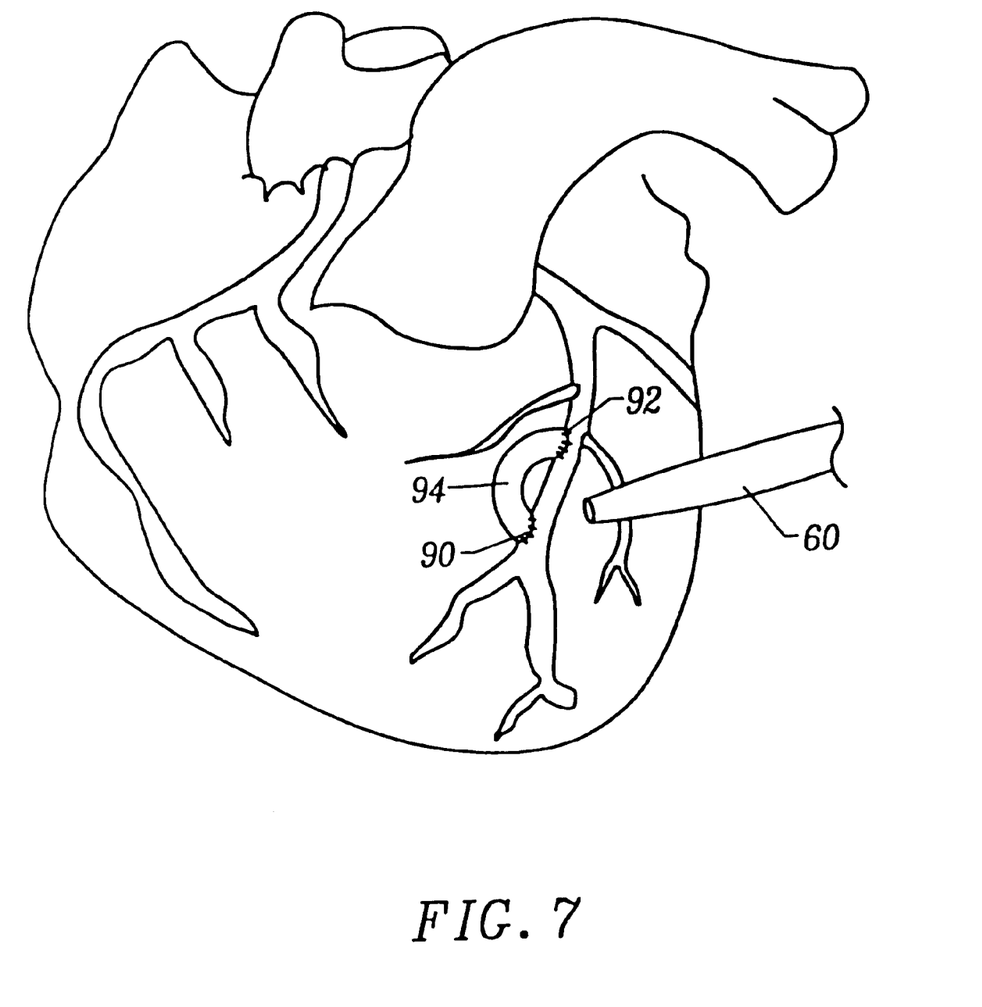
FIG. 7 illustrates treatment of a heart bypass graft according to the methods of the present invention.

Referring now to FIG. 7, use of a probe 60 for treating anastomotic junctions 90 and 92 formed at either end of a cardiac bypass graft is illustrated. The bypass graft 94 may be implanted using conventional open surgical techniques, and the probe 60 introduced through the opening in the sternum to perform the methods of the present invention. Alternatively (and not illustrated) intravascular catheters can be used to treat the anastomotic junctions following catheter-based techniques for performing cardiopulmonary bypass, such as those presently commercialized by Heartport, Inc.

Figure 8:
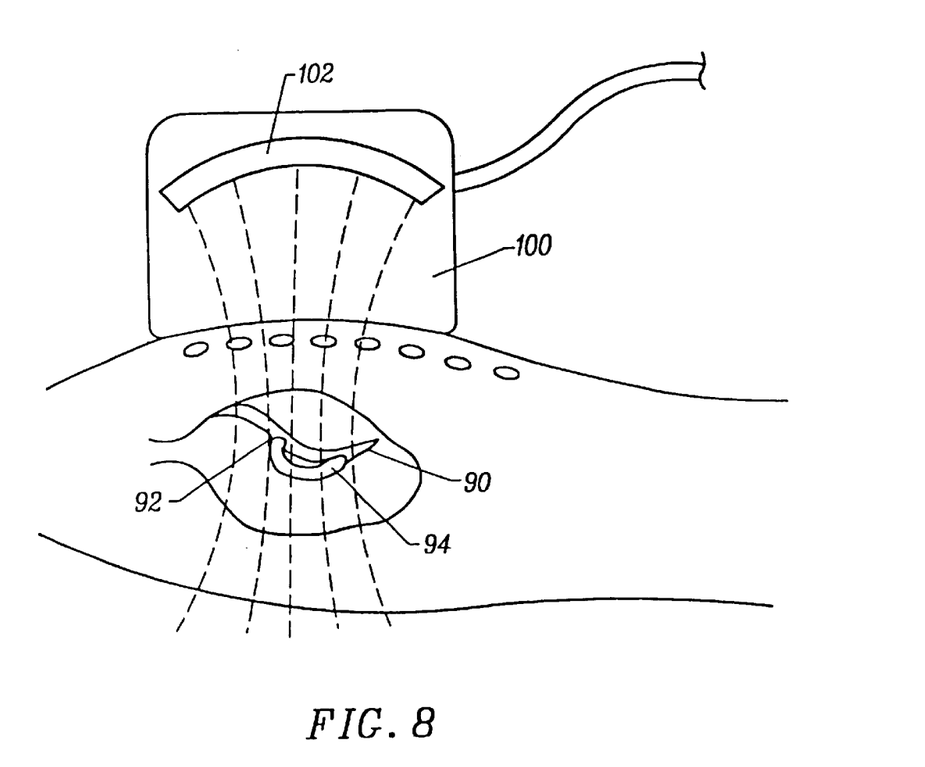
FIG. 8 illustrates an alternative approach for treatment of a heart bypass graft according to the methods of the present invention.

Use of an external skin probe 100 for treating the anastomotic junctions 90 and 92 of a cardiac bypass graft 94 is illustrated in FIG. 8. The probe will usually contain an ultrasonic array 102 configured to focus the energy through tissue overlying the heart so that the vibrational energy can be delivered in a focused manner to each of the anastomotic junctions. Methods and devices suitable for performing such external vibrational treatment protocols are described in copending application Ser. No. 09/343,950 filed Jun. 30, 1999, (Attorney Docket No. 17148-003000/PSI-030), the full disclosure of which is incorporated herein by reference.

Figure 9:
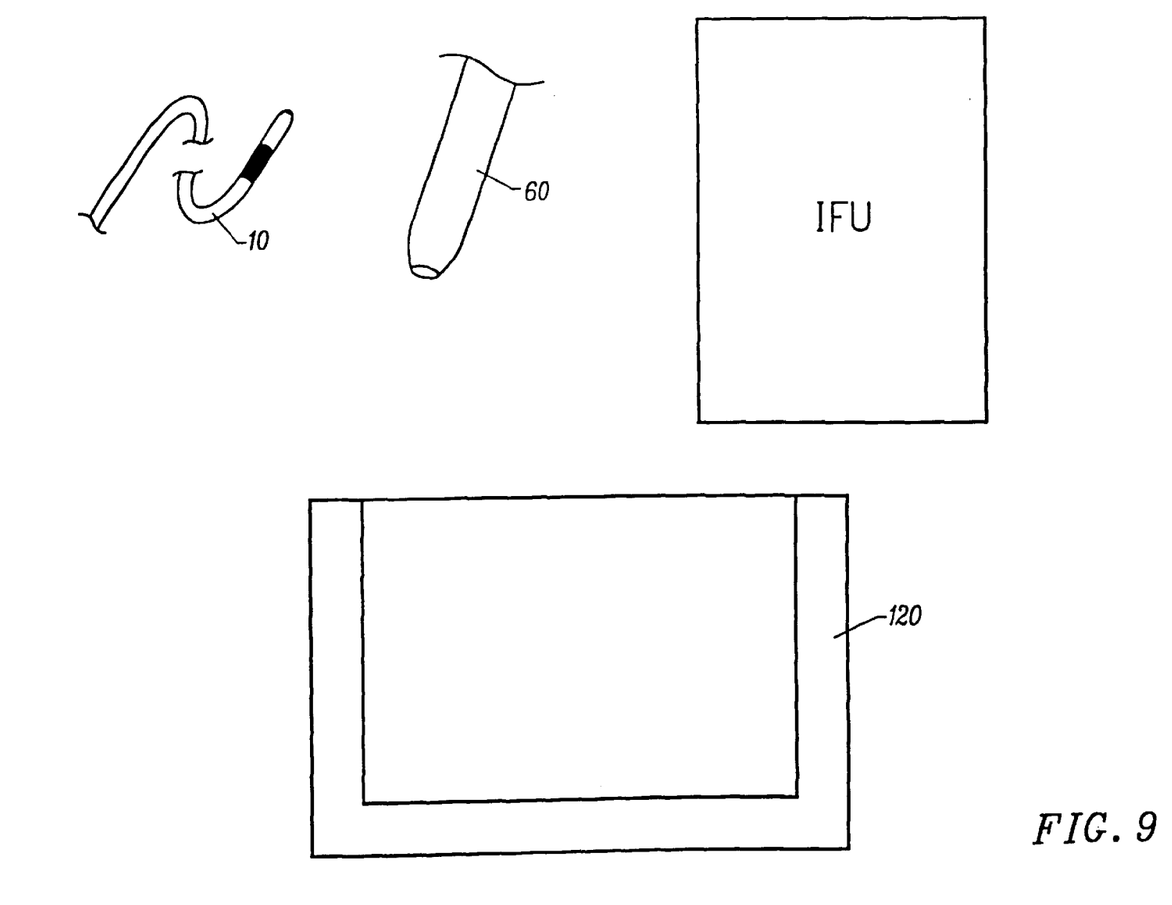
FIG. 9 illustrates a kit constructed in accordance with the principles of the present invention.

Referring now to FIG. 9, the present invention comprises kits including at least one of a catheter 10 and probe 60 for applying vibrational energy according to the methods described above. The kits will further comprise instructions for use IFU setting forth methods according to the present invention. The kit components, including at least one of the catheter 10 and the probe 60, and the instructions for use will typically be packaged together in a conventional medical device package 120, typically a box, tube, tray, pouch, or the like. Preferably, at least some of the kit components will be maintained in a sterile condition within the kit.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for recanalizing an anastomotic junction of a vascular fistula or graft, said method comprising:
    recanalizing an anastomotic junction that has become occluded; and
    exposing the recanalized junction to vibrational energy at a mechanical index and for a time sufficient to inhibit hyperplasia.

2. A method as in claim 1, wherein recanalizing of the anastomotic junction comprises angioplasty or atherectomy.

3. A method as in claim 1, wherein the vibrational energy does not cause significant cavitation in a wall of the blood vessel.

4. A method as in claim 1, wherein the vibrational energy causes a temperature rise below 10° C. in the wall of the blood vessel.

5. A method as in claim 1, wherein vascular smooth muscle cells at least mostly remain viable but in a quiescent state in the neointimal layer after exposure to the vibrational energy.

6. A method as in claim 1, wherein migration of vascular smooth muscle cells into the neointimal layer is not substantially inhibited.

7. A method as in claim 1, wherein viability of vascular smooth muscle cells in a medial layer of the blood vessel is not significantly inhibited.

8. A method as in claim 1, wherein the vibrational energy has a frequency in the range from 20 kHz to 5 MHz.

9. A method as in claim 8, wherein the intensity is in the range from 0.01 W/cm$^2$ to 100 W/cm$^2$.

10. A method as in claim 9, wherein the frequency and intensity are selected to produce a mechanical index at the neointimal wall in the range from 0.1 to 50.

11. A method as in claim 1, wherein the vibrational energy is directed against the anastomotic junction with a pulse repetition frequency (PRF) in the range from 10 Hz to 10 kHz.

12. A method as in claim 1, wherein the energy is directed against the anastomotic junction with a duty cycle in the range from 0.1 to 100 percent.

13. A method as in claim 1, wherein the anastomotic junction is between an artery and a vein in an arterio-venous fistula.

14. A method as in claim 1, wherein the anastomotic junction is between a graft and a vein in an arterio-venous graft.

15. A method as in claim 1, wherein the anastomotic junction is between a graft and a coronary artery in a coronary artery bypass graft.

* * * * *